United States Patent [19]

Hagen et al.

[11] Patent Number: 5,565,408
[45] Date of Patent: Oct. 15, 1996

[54] CYANOQUINOLINE COMPOUNDS

[75] Inventors: Helmut Hagen, Frankenthal; Juergen Pfister, Speyer; Gunter Brill, Hassloch; Gerhard Nilz, Dannstadt-Schauernheim; Bruno Wuerzer, Otterstadt; Karl-Otto Westphalen, Speyer, all of Germany

[73] Assignee: BASF Aktiengesellschaft, Ludwigshafen, Germany

[21] Appl. No.: 423,325

[22] Filed: Apr. 17, 1995

Related U.S. Application Data

[63] Continuation of Ser. No. 13,232, Feb. 3, 1993, abandoned, which is a continuation of Ser. No. 692,840, Apr. 29, 1991, abandoned.

[30] Foreign Application Priority Data

May 3, 1990 [DE] Germany .......................... 40 14 171.3

[51] Int. Cl.[6] .................. C07D 215/28; C07D 215/26; A01N 43/40
[52] U.S. Cl. .................. 504/104; 504/105; 504/106; 546/153; 546/161; 546/178
[58] Field of Search .................. 71/92, 94; 504/104, 504/105, 106; 546/153, 161, 178

[56] References Cited

U.S. PATENT DOCUMENTS

| | | | |
|---|---|---|---|
| 2,507,146 | 5/1950 | Dickey et al. | 546/155 |
| 2,991,285 | 7/1961 | Feely | 546/157 |
| 4,362,876 | 12/1982 | Vacek | 546/155 |
| 4,456,468 | 6/1984 | Martin | 504/104 |
| 4,488,898 | 12/1984 | Förg et al. | 504/104 |
| 4,490,167 | 12/1984 | Pissiotas et al. | 504/104 |
| 4,496,569 | 1/1985 | Wright | 71/92 |
| 4,496,725 | 1/1985 | McCarthy et al. | 544/184 |
| 4,497,651 | 2/1985 | Hagen et al. | 71/94 |
| 4,511,393 | 4/1985 | Hagen et al. | 71/92 |
| 4,530,716 | 7/1985 | Martin et al. | 504/104 |
| 4,540,786 | 9/1985 | Wright | 71/92 |
| 4,623,727 | 11/1986 | Hubele | 546/178 |
| 4,851,031 | 7/1989 | Bellucci et al. | 504/105 |
| 4,920,128 | 4/1990 | Bell et al. | 514/293 |
| 4,927,935 | 5/1990 | Hackenberger et al. | 546/157 |
| 4,933,447 | 6/1990 | Koono et al. | 544/128 |
| 5,030,269 | 7/1991 | Barton et al. | 504/104 |
| 5,035,736 | 7/1991 | Hagen et al. | 71/98 |
| 5,059,240 | 10/1991 | Hagen et al. | 71/94 |

FOREIGN PATENT DOCUMENTS

| | | |
|---|---|---|
| 126487 | 11/1984 | European Pat. Off. . |
| 159290 | 3/1985 | European Pat. Off. . |
| 258184 | 3/1988 | European Pat. Off. . |
| 318225 | 5/1989 | European Pat. Off. . |
| 354994 | 2/1990 | European Pat. Off. . |
| 356971 | 3/1990 | European Pat. Off. . |
| 2363459 | 6/1975 | Germany . |
| 1170955 | 8/1975 | Germany . |
| 1207771 | 3/1969 | United Kingdom . |
| 1398066 | 6/1975 | United Kingdom . |
| 1467225 | 3/1977 | United Kingdom . |
| WO84/01947 | 11/1982 | WIPO . |

OTHER PUBLICATIONS

Mehnert et al., Archiv Der Pharmazie, vol. 321, No. 12, Dec. 1988, pp. 891–896.
Srivastava et al., Ind. J. of Chem., vol. 28B, No.7, Jul. 1989, pp. 562–573.
Leardini et al., Gazz. Chimica Italiana, vol. 119, 1989, pp. 637–641.
Adams et al., Synth. Comm. 20(3), pp. 469–475 (1990).

*Primary Examiner*—James H. Reamer
*Assistant Examiner*—Keith MacMillan
*Attorney, Agent, or Firm*—Keil & Weinkauf

[57] ABSTRACT

Cyanoquinoline compounds Ia or Ib

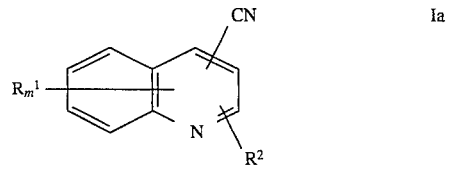

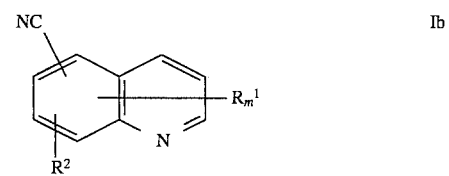

where $R^1$ is $CH=C(CN)_2$; $CH=N-N=CH-$(5-quinolyl); methylsulfonyl; $CH=NOH$; halogen; hydroxyl; nitro; cyano; unsubstituted or substituted $C_1-C_4$-alkyl, $C_1-C_4$-alkoxy or $C_1-C_4$-alkylthio, pyrrolidinyl; piperidinyl; morpholinyl; thiomorpholinyl; unsubstituted or substituted phenyl, phenoxy, phenylthio, phenyldithiolyl, phenylsulfonyl or pyrrolyl;

m is 0, 1, 2 or 3;

$R^2$ is hydrogen; hydroxyl; halogen; $C_1-C_4$-alkoxy; $-NR^3R^4$; $-NR^5-CXR^6$ or $-N=CR^7R^8$;

$R^3$ is hydrogen or unsubstituted or substituted $C_1-C_4$-alkyl;

$R^4$ is a radical $R^3$; $C_1-C_4$-alkylamino; di-$C_1-C_4$-alkylamino; substituted $C_1-C_4$-alkyl; $CH=N-$(3-cyano-2-quinolinyl); or $R^3$ and $R^4$ together form $C_4$- or $C_3$-alkylene which may be interrupted by a hetero atom, or unsubstituted or substituted 1,3-butadienyl;

$R^5$ and $R^7$ are each hydrogen or $C_1-C_4$-alkyl;

$R^6$ and $R^8$ are each a radical $R^5$; substituted $C_1-C_4$-alkyl; $C_3-C_7$-cycloalkyl; $C_1-C_4$-alkoxycarbonyl; unsubstituted or substituted phenyl or unsubstituted or substituted amino, and X is oxygen or sulfur, processes for their preparation and herbicides which contain them.

7 Claims, No Drawings

CYANOQUINOLINE COMPOUNDS

This application is a continuation of application Ser. No. 08/013,232, filed on Feb. 3, 1993, now abandoned, which is a continuation of application Ser. No. 07/692,840, filed on Apr. 29, 1991, now abandoned.

The present invention relates to cyanoquinoline compounds of the general formula Ia or Ib

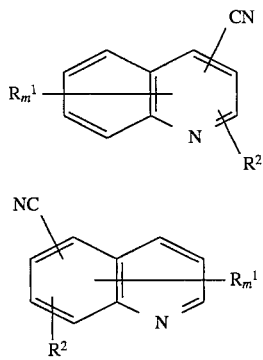

where

- $R^1$ is $CH=C(CN)_2$; $CH=N—N=CH$—(5-quinolinyl); methylsulfonyl; $CH=NOH$; halogen; hydroxyl; nitro; cyano; $C_1$–$C_4$-alkyl which may be monosubstituted by cyano, hydroxyl, carboxyl or $C_1$–$C_4$-alkoxycarbonyl; $C_1$–$C_4$-haloalkyl; $C_1$–$C_4$-alkoxy; $C_1$–$C_4$-haloalkoxy; $C_1$–$C_4$-alkylthio which may be monosubstituted by $C_1$–$C_4$-alkoxycarbonyl; pyrrolidinyl; piperidinyl; morpholinyl; thiomorpholinyl;

phenyl, phenoxy, phenylthio, phenyldithiolyl, phenylsulfonyl or pyrrolyl which may carry from one to three of the following groups: halogen, $C_1$–$C_4$-alkyl, $C_1$–$C_4$-haloalkyl, $C_1$–$C_4$-alkoxy, $C_1$–$C_4$-alkylthio, $C_2$–$C_4$-alkenyl, nitro, amino, nitro-$C_2$–$C_4$-alkenyl and/or benzyl;

m is 0, 1, 2 or 3, and the radicals $R^1$ may be different when m is 2 or 3;

- $R^3$ is hydrogen; hydroxyl; halogen, $C_1$–$C_4$-alkoxy; $—NR^3R^4$; $—NR^5—CXR^6$ or $—N=CR^7R^8$;

- $R^3$ is hydrogen or $C_1$–$C_4$-alkyl which may carry from one to five halogen atoms and/or one of the following groups: hydroxyl, $C_1$–$C_4$-alkoxy, $C_1$–$C_4$-haloalkoxy, $C_1$–$C_4$-alkylthio, amino, $C_1$–$C_4$-alkylamino or di-$C_1$–$C_4$-alkylamino;

- $R^4$ is one of the groups stated for $R^3$; $C_1$–$C_4$-alkylamino; di-$C_1$–$C_4$-alkylamino; $C_1$–$C_4$-alkyl which carries one of the following radicals: $C_1$–$C_4$-alkoxycarbonyl, 1-pyrrolidinyl or 1-imidazolyl; $CH=N$—(3-cyano-2-quinolinyl);

or $R^3$ and $R^4$ together form a $C_4$- or $C_5$-alkylene chain which may be interrupted by an oxygen or nitrogen member, where the nitrogen atom in turn may carry a $C_1$–$C_4$-alkyl or amino-$C_1$–$C_4$-alkyl group, or a 1,3-butadienyl chain which may carry one or two of the radicals stated for $R^1$ or formyl;

- $R^5$ is hydrogen or $C_1$–$C_4$-alkyl;

- $R^6$ is one of the groups stated for $R^5$; $C_1$–$C_4$-alkyl which carries one of the following radicals: $C_1$–$C_4$-alkoxy, $C_1$–$C_4$-alkylcarbonyl or $C_1$–$C_4$-alkoxycarbonyl; $C_3$–$C_7$-cycloalkyl; $C_1$–$C_4$-alkoxycarbonyl; a phenyl ring which may carry from one to three of the groups stated for $R^1$; amino; $C_1$–$C_4$-alkylamino; di-$C_1$–$C_4$-alkylamino; $C_3$–$C_7$-cycloalkylamino or phenylamino, where the aromatic ring may carry from one to three of the groups stated for $R^1$;

- X is oxygen or sulfur;

- $R^7$ is one of the groups stated for $R^5$;

- $R^8$ is one of the groups stated for $R^6$ and $R^2$ is not hydrogen, hydroxyl or amino when m is 0 and $R^1$ is not methoxy and m is 1 when $R^2$ is hydrogen, and the environmentally compatible salts of the compounds Ia and Ib, provided that these compounds contain a basic nitrogen substituent or an acidic hydroxyl substituent.

The present invention furthermore relates to processes for the preparation of compounds Ia and Ib and herbicides which contain the 2-(4-hetaryloxy)- or 2-(4-aryloxy)-phenoxyacetic or -propionic acid derivatives and/or cyclohexenone derivatives as herbicidal active ingredients and cyanoquinolines IA and IB as antidotes

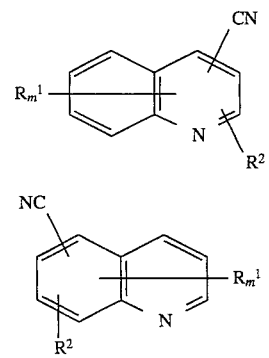

where $R^1$ and $R^2$ and the index have the abovementioned meanings and further $R^2$ is hydrogen, hydroxyl or amino when m is 0, and $R^1$ is methoxy when m is 1 and $R^2$ is hydrogen, and methods for selectively controlling undesirable plant growth using these herbicides.

Herbicidal active ingredients from the group consisting of the 2-(4-hetaryloxy)- or 2-(4-aryloxy)phenoxyacetic acid derivatives of the formula IX

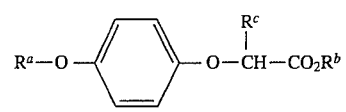

where

- $R^a$ is a phenyl ring, a pyridyl ring, a benzoxazyl radical, a benzothiazyl radical or a benzopyrazinyl radical, where these aromatic ring systems may carry up to two of the following radicals: halogen, nitro, $C_1$–$C_4$-alkyl, $C_1$–$C_4$-haloalkyl and/or $C_1$–$C_4$-haloalkoxy,

- $R^b$ is hydrogen, $C_1$–$C_4$-alkyl or one equivalent of a plant-tolerated cation and

- $R^c$ is hydrogen or methyl, are known from the literature, for example from DE-A-22 23 894, DE-A-24 33 067, DE-A-25 76 251, DE-A-30 04 770, BE-A-868 875 and BE-A-858 618.

They are used for controlling undesirable plants from the Gramineae family. However, the toleration of these substances by crops varies from commercially acceptable to nontolerated, depending on the substituents and application rate.

The same situation applies to cyclohexenone derivatives of the formula X

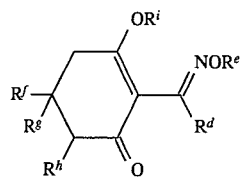

where

R$^d$ is C$_1$–C$_4$-alkyl;

R$^e$ is C$_1$–C$_4$-alkyl, C$_3$- or C$_4$-alkenyl, C$_3$- or C$_4$-alkynyl, C$_3$- or C$_4$-haloalkylene or thenyl, which may be substituted by a halogen atom; C$_3$- or C$_4$-alkenyl which carries a phenyl radical which may carry from one to three of the following radicals: halogen, C$_1$–C$_4$-alkyl, C$_1$–C$_4$-alkoxy, C$_1$–C$_4$-haloalkyl and/or C$_1$–C$_4$-haloalkoxy;

R$^f$ is C$_1$–C$_4$-alkyl which may be monosubstituted or di-substituted by C$_1$–C$_4$-alkylthio or C$_1$–C$_4$-alkoxy; a 5-membered or 6-membered saturated or monounsaturated ring system which, in addition to carbon members, may contain an oxygen or sulfur atom or a sulfoxyl or sulfonyl group, and this ring may carry up to three of the following radicals: hydroxyl, halogen, C$_1$–C$_4$-alkyl, C$_1$–C$_4$-haloalkyl, C$_1$–C$_4$-alkoxy and/or C$_1$–C$_4$-alkylthio; a 10-membered saturated or monounsaturated heterocyclic structure which contains two oxygen or sulfur atoms and may be substituted by up to three C$_1$–C$_4$-alkyl groups and/or methoxy groups; a phenyl, pyridyl, thiazolyl, pyrazolyl, pyrrolyl or isoxazolyl radical which may carry up to three of the following groups: C$_1$–C$_4$-alkyl, C$_1$–C$_4$-haloalkyl, C$_1$–C$_4$-alkoxy, C$_1$–C$_4$-alkylthio, C$_3$–C$_6$-alkenyloxy, C$_3$–C$_6$-alkynyloxy, C$_1$–C$_4$-alkoxy-C$_1$–C$_3$-alkyl, C$_1$–C$_4$-dialkoxy-C$_1$–C$_3$-alkyl, formyl, halogen and/or benzoylamino;

R$^g$ is hydrogen, hydroxyl or, if R$^f$ is C$_1$–C$_6$-alkyl, a C$_1$–C$_6$-alkyl group;

R$^h$ is hydrogen, cyano, halogen, C$_1$–C$_4$-alkoxycarbonyl or C$_1$–C$_4$-alkylketoxime and R$^i$ is hydrogen or one equivalent of an environmentally compatible cation.

They are likewise described in the literature (e.g. EP-A 228 598, EP-A 230 235, EP-A 238 021, U.S. Pat. No. 4,432,786, DE-A 24 39 104) as herbicides and are used predominantly for controlling undesirable grasses in dicotyledon crops and in grasses which do not belong to the Gramineae family. Depending on the structure of the substituents and the application rate, compounds from this group can also be used for selectively controlling undesirable grasses in gramineous crops, such as wheat and rice.

It is an object of the present invention to provide compounds which reduce the disadvantages which occur when the abovementioned herbicides of the formulae IX and X are used, at least to such an extent that the harvest yield of the crops is reduced to an insignificant extent, if at all.

The novel compounds Ia and Ib are obtainable by various methods. Substituted cyanoquinolines are obtained, for example, by condensation of unsubstituted or substituted o-aminobenzaldehydes with cyanoacetic acid derivatives (G. Jones in Chemistry of Heterocyclic Compounds, Vol. 32/1, Wiley and Sons, New York/London, pages 180–190) or by reaction of haloquinolines (R. K. Smalley in Chemistry of Heterocyclic Compounds, Vol. 32/1, Wiley and Sons, New York/London, pages 319–521) with copper(I) cyanide (P. Kurtz in Methoden der organischen Chemie (Houben-Weyl), Vol. VIII, pages 302–304, G. Thieme, Stuttgart, 1952). Another method of obtaining these compounds is the reaction of nitroquinolines with cyanoacetic esters (M. Yamazaki et al., Chem. Pharm. Bull. 29 (1981), 1286, 1292 and 1328; Chem. Pharm. Bull. 30 (1982), 851; Chem. Pharm. Bull. 33 (1985), 1360). A crop protection action is not described in the prior art.

We have found that this object is achieved and that the cyanoquinolines Ia and Ib are obtained, for example according to the literature cited at the outset, by reacting a haloquinoline of the formula IIa or IIb with an inorganic cyanide of the formula III in the presence of an organic base, such as pyridine or quinoline.

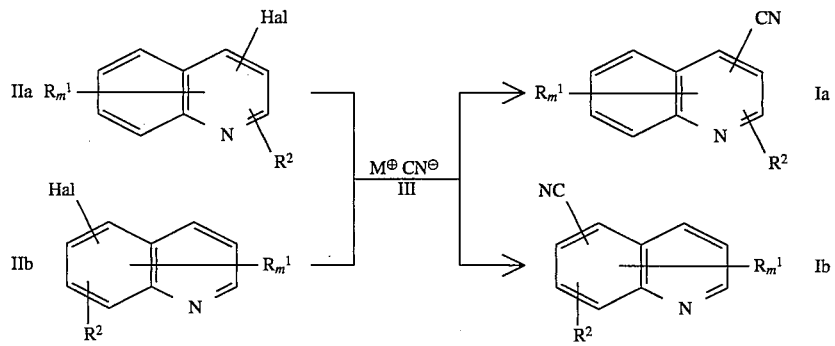

In the formulae IIa and IIb, Hal is a halogen atom, such as fluorine, chlorine, bromine or iodine, preferably chlorine or bromine.

M$^\oplus$ in formula III is one equivalent of a metal cation, such as copper(I), silver(I) and zinc(II), preferably copper(I), ions.

In particular, pyridine, quinoline, dimethylformamide, dimethyl sulfoxide and N-methylpyrrolidone are used as solvents.

The reaction can be carried out continuously or batchwise under atmospheric, superatmospheric or reduced pressure by the conventional methods. The reaction temperature is in general from 20° to 400° C., in particular from 150° to 200° C., advantageously in the boiling range of the solvent.

The starting materials IIa or IIb and III are usually used in a stoichiometric ratio. However, an excess of one or other may be quite advantageous in specific cases.

Compounds of the formula Ia in which $R^2$ is hydroxyl or amino are particularly advantageously obtained by subjecting an o-aminobenzaldehyde IV to a fusion reaction with an acetonitrile Va or Vb in a conventional manner in an inert organic solvent in the presence of a base.

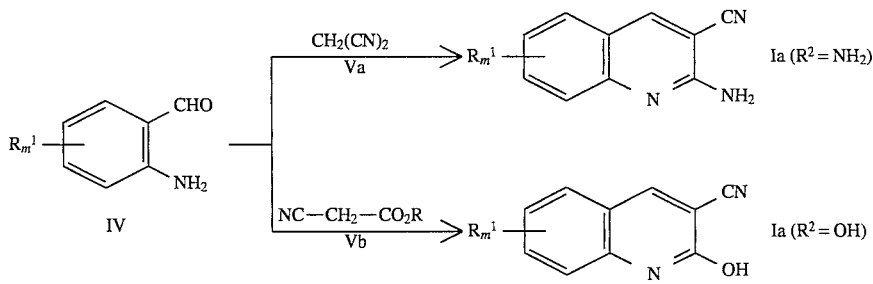

In formula Vb, R is alkyl, such as methyl, ethyl, propyl, 1-methylethyl, butyl, 1-methylpropyl, 2-methylpropyl or 1,1-dimethylethyl, preferably methyl or ethyl.

The reaction can be carried out continuously or batchwise under atmospheric, superatmospheric or reduced pressure by the conventional methods. The reaction temperature is in general from 20° to 200° C., in particular from 50° to 150° C., advantageously in the boiling range of the solvent.

Examples of suitable solvents are aliphatic and aromatic hydrocarbons and chlorohydrocarbons, such as petroleum ether, benzene, toluene, xylene, gasoline, dichloromethane, chloroform, tetrachloromethane, 1,2-dichloroethane, chlorobenzene, relatively high boiling ethers, such as tetrahydrofuran or dioxane, and nitriles, such as acetonitrile and propionitrile.

Particularly suitable bases are aliphatic, aromatic or heterocyclic amines, such as triethylamine, dimethylamine, diisopropylamine, piperidine, dimethylaniline, dimethylbenzylamine, pyridine and 4-dimethylaminopyridine, hydroxides of alkali metals and of alkaline earth metals, such as sodium hydroxide, potassium hydroxide and calcium hydroxide, alcoholates of alkali metals and of alkaline earth metals, such as sodium methylate, sodium ethylate, calcium methylate and potassium tert-butylate, and alkali metal and alkaline earth metal hydrides, such as sodium hydride, potassium hydride and calcium hydride.

The compounds Ia and Ib in which $R^2$ is amino are also obtained, however, by reacting a nitroquinoline VIa or VIb with an acetonitrile of the formula Vb as defined above in a conventional manner in an inert organic solvent in the presence of a base.

The starting materials V and VI are usually used in a ratio of from 1:1 to 10:1, in particular from 2:1 to 5:1, with from 1 to 10, in particular from 1 to 5, mole equivalents, based on VI, of a base.

The reaction can be carried out continuously or batchwise under atmospheric, superatmospheric or reduced pressure by the conventional methods. The reaction temperature is in general from 0° to 100° C., in particular from 15° to 60° C.

Dipolar aprotic compounds, such as dimethylformamide, N-methylpyrrolidone or dimethyl sulfoxide, can be used as solvents.

Bases which are used in particular are hydroxides of alkali metals and of alkaline earth metals, e.g. sodium hydroxide, potassium hydroxide and calcium hydroxide, alcoholates of alkali metals and of alkaline earth metals, for example sodium methylate, sodium ethylate, calcium methylate and potassium tert-butylate, alkali metal or alkaline earth metal hydrides, for example sodium hydride, potassium hydride or calcium hydride, alkali metal amides, such as sodium amide or potassium amide, and alkali metal cyanides, such as sodium cyanide and potassium cyanide.

In view of the intended use of the compounds Ia and Ib, preferred substituents are the following radicals:

$R^1$ is $CH=C(CN)_2$; $CH=N-N-CH-(5$-quinolyl), methylsulfonyl, $CH=NOH$, halogen, such as fluorine, chlorine, bromine or iodine, in particular chlorine or bromine, hydroxyl, alkyl, such as methyl, ethyl, propyl, 1-methylethyl, butyl, 1-methylpropyl, 2-methylpropyl or 1,1-dimethylethyl, in particular methyl or ethyl, which may be monosubstituted by cyano, hydroxyl, carboxyl or $C_1$-$C_4$-alkoxycarbonyl, in particular methoxycarbonyl, ethoxycarbonyl or 1-methylethoxycarbonyl, haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl, in particular trifluoromethyl or trichloromethyl, alkoxy, such as methoxy, ethoxy,

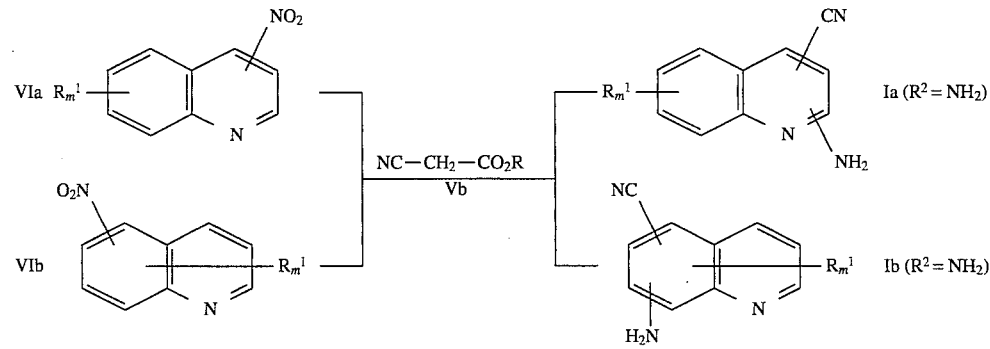

propoxy, 1-methylethoxy, butoxy, 1-methylpropoxy, 2-methylpropoxy or 1,1-dimethylethoxy, in particular methoxy or ethoxy, haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular 2,2,2-trifluoroethoxy, alkylthio, such as methylthio, ethylthio, propylthio, 1-methylethylthio, butylthio, 1-methylpropylthio, 2-methylpropylthio, or 1,1-dimethylethylthio, in particular methylthio or butylthio, which may be monosubstituted by $C_1$–$C_4$-alkoxycarbonyl, in particular as stated above, pyrrolidinyl, piperidinyl, morpholinyl, thiomorpholinyl, phenyl, phenoxy, phenylthio, phenyldithiolyl (—S—S-phenyl) or pyrrolyl, where these substituents may carry from one to three of the following radicals: alkyl as stated above, in particular methyl, haloalkyl as stated above, in particular trifluoromethyl, alkoxy as stated above, in particular methoxy, ethoxy or 1-methylethoxy, alkylthio as stated above, in particular methylthio, alkenyl, in particular ethenyl, 1-propenyl, 2-propenyl, 1-butenyl, 2-butenyl, 3-butenyl, 1-methyl-1-propenyl, 2-methyl-1-propenyl, 1-methyl-2-propenyl or 2-methyl-2-propenyl, nitro, amino, nitroalkenyl, in particular 2-nitroethenyl, and/or benzyl, m is 0, 1, 2 or 3, and the radicals $R^1$ may be different when m is 2 or 3, $R^2$ is hydrogen, hydroxyl, halogen as stated for $R^1$, in particular chlorine or bromine, alkoxy as stated for $R^1$, in particular methoxy or ethoxy, —$NR^3R^4$, —$NR^5$—$CXR^6$ or —N=$CR^7R^8$, $R^3$ is hydrogen, alkyl as stated for $R^1$, in particular methyl or ethyl, which may carry from one to five of the halogen atoms stated in general and in particular for $R^1$ and/or one of the following groups: hydroxyl or alkoxy as stated for $R^1$, in particular fluorine or chlorine, haloalkoxy as stated for $R^1$, in particular 2,2,2-trifluoroethoxy, alkylthio as stated for $R^1$, in particular methylthio or butylthio, or amino which may carry one or two of the alkyl radicals stated for $R^1$, where these alkyl radicals may be different in the case of disubstituted amino, in particular dimethylamino, $R^4$ is one of the groups stated in general and in particular for $R^3$, amino which carries one or two of the alkyl radicals stated for $R^1$, where these alkyl radicals may be different in the case of disubstituted amino, in particular dimethylamino, alkyl as stated for $R^1$, in particular methyl or ethyl, which may carry one of the following radicals: alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl, in particular methoxycarbonyl, 1-pyrrolidinyl or 1-imidazolyl or CH=N—(3-cyano-2-quinolinyl), or $R^3$ and $R^4$ together form a butylene or pentylene chain which may be interrupted by a nitrogen atom, such as —$CH_2CH_2$—NH—$CH_2CH_2$— or —$CH_2CH_2$—NH—$CH_2CH_2CH_2$—, where the nitrogen atom in turn may carry an alkyl group as stated for $R^1$, in particular methyl or ethyl, and this alkyl group in turn may carry an amino group, in particular in the 2-position, 1,3-butadienyl which may carry one or two of the radicals stated for $R^1$, in particular methyl, or formyl, $R^5$ is hydrogen or alkyl as stated for $R^1$, in particular methyl, $R^6$ is one of the groups stated for $R^5$, alkyl as stated for $R^1$, in particular methyl or 2,2-dimethylpropyl, which may carry one of the following radicals: alkoxy as stated for $R^1$, in particular methoxy, cycloalkyl, such as cyclopropyl, cyclobutyl, cyclopentyl, cyclohexyl or cycloheptyl, alkoxycarbonyl as stated above and in general and in particular for $R^4$, phenyl which may carry from one to three of the radicals stated in general and in particular for $R^1$, amino which may carry one or two of the alkyl radicals stated for $R^1$, where these radicals may be different in the case of disubstituted amino, in particular methylamino or ethylamino, phenylamino, where the phenyl ring in turn may carry from one to three of the radicals stated in general and in particular for $R^1$, X is oxygen or sulfur, $R^7$ is one of the groups stated in general and in particular for $R^5$, $R^8$ is one of the groups stated in general and in particular for $R^6$, and $R^2$ is not hydrogen, hydroxyl or amino when m is 0 and $R^1$ is not methoxy when $R^2$ is hydrogen and m is 1, and the agriculturally usable salts of the compounds Ia and Ib, provided that these compounds contain a basic nitrogen substituent or an acidic hydroxyl substituent.

Suitable salts of the compounds of the formulae IA and IB are agriculturally usable salts, for example alkali metal salts, in particular the potassium or sodium salt, alkaline earth metal salts, in particular the calcium, magnesium or barium salt, manganese salts, copper salts, zinc salts or iron salts and ammonium, phosphonium, sulfonium or sulfoxonium salts, for example ammonium salts, tetraalkylammonium salts, benzyltrialkylammonium salts, trialkylsulfonium salts or trialkylsulfoxonium salts.

Specific examples of herbicidal hetaryloxy- or aryloxyphenoxyacetic acid derivatives of the formula IX whose toleration by crops can be improved by substituted cyanoquinolines of the formulae IA and IB are shown in the Table A below.

TABLE A $$R^a-O-\phenyl-O-CH(R^c)-CO_2R^b$$

| No. | $R^a$ | $R^b$ | $R^c$ | References |
|---|---|---|---|---|
| IX.1 | 3,4-dichlorophenyl | $CH_3$ | $CH_3$ | DE-A 22 23 894 |
| IX.2 | 5-trifluoromethyl-2-pyridyl | n-$C_4H_9$ | $CH_3$ | BE-A 868 875 |
| IX.3 | 4-chloro-2-methylbenzoxazol-? | $C_2H_5$ | $CH_3$ | BE-A 858 618 |
| IX.4 | 3-chloro-5-trifluoromethyl-2-pyridyl | $CH_3$ | $CH_3$ | BE-A 868 875 |
| IX.5 | 6-chloroquinoxalin-2-yl | $C_2H_5$ | $CH_3$ | DE-A 30 04 770 |

Specific examples of cyclohexenones of the formula X whose toleration by crops can be improved by the compounds of the formulae Ia and Ib are shown in Table B below.

TABLE B

[Structure: cyclohexanone ring with OR$^i$, =NOR$^e$/R$^d$ group, =O, R$^f$, R$^g$, R$^h$ substituents]

| No. | R$^d$ | R$^e$ | R$^f$ | R$^g$ | R$^h$ | R$^i$ | Reference |
|---|---|---|---|---|---|---|---|
| X.1 | C$_3$H$_7$ | CH$_2$CH=CH$_2$ | CH$_3$ | CH$_3$ | CO$_2$CH$_3$ | Na | DE-A 2 439 104 |
| X.2 | C$_3$H$_7$ | CH$_2$CH$_3$ | CH$_2$CH(CH$_3$)SCH$_2$CH$_3$ | H | H | H | DE-A 2 822 304 |
| X.3 | C$_2$H$_5$ | CH$_2$CH=CHCl | CH$_2$CH(CH$_3$)SCH$_2$CH$_3$ | H | H | H | US-A 4 440 566 |
| X.4 | C$_3$H$_7$ | CH$_2$CH=CHCl | CH$_2$CH(CH$_3$)SCH$_2$CH$_3$ | H | H | H | US-A 4 440 566 |
| X.5 | C$_3$H$_7$ | C$_2$H$_5$ | [tetrahydrothiopyran-methyl] | H | H | H | EP-A 71 707 |
| X.6 | C$_2$H$_5$ | C$_2$H$_5$ | [tetrahydrothiopyran-methyl] | H | H | H | EP-A 71 707 |
| X.7 | CH$_3$ | CH$_2$CH=CHCH$_3$ | [tetrahydrothiopyran-methyl] | H | H | H | EP-A 71 707 |
| X.8 | C$_3$H$_7$ | C$_2$H$_5$ | [tetrahydropyran-methyl] | H | H | H | EP A 71 707 |
| X.9 | C$_2$H$_5$ | CH$_2$CH=CHCl | [tetrahydropyran-methyl] | H | H | H | EP-A 142 741 |
| X.10 | C$_3$H$_7$ | C$_2$H$_5$ | [pyridinyl-methyl] | H | H | H | EP-A 66 195 |

TABLE B-continued structure: cyclohexenone with $R^f$, $R^g$, $R^h$ substituents, $OR^i$ group, and $=NOR^e$ oxime group with $R^d$

| No. | $R^d$ | $R^e$ | $R^f$ | $R^g$ | $R^h$ | $R^i$ | Reference |
|---|---|---|---|---|---|---|---|
| X.11 | $C_2H_5$ | $C_2H_5$ | 4-CH$_3$-C$_6$H$_4$- | H | H | H | DE-A 24 39 104 |
| X.12 | $C_2H_5$ | $CH_2CH=CHCH_3$ | 4-C$_2$H$_5$-C$_6$H$_4$- | H | H | H | DE-A 38 08 072 |
| X.13 | $C_2H_5$ | $C_2H_5$ | 2,4,6-tri-CH$_3$-C$_6$H$_2$- | H | H | H | EP-A 880 301 |
| X.14 | $C_3H_7$ | $CH_2CH=CHCl$ | 4-CH$_3$-cyclohexyl | H | H | H | EP-A 88 299 |
| X.15 | $C_3H_7$ | $CH_2CH=CHCH_3$ | 4-CH$_3$-cyclohexyl | H | H | H | EP-A 88 299 |
| X.16 | $C_2H_5$ | $CH_2CH=CHCH_3$ | 3-CH(CH$_3$)$_2$-5-CH$_3$-isoxazolyl | H | H | H | EP-A 238 021 |
| X.17 | $C_3H_7$ | $CH_2CH=CHCH_3$ | 3-CH(CH$_3$)$_2$-5-CH$_3$-isoxazolyl | H | H | H | EP-A 238 021 |

TABLE B-continued

[Structure: cyclohexanone with OR$^i$ at position, =NOR$^e$ with R$^d$ substituent, and R$^f$, R$^g$, R$^h$ substituents]

| No. | R$^d$ | R$^e$ | R$^f$ | R$^g$ | R$^h$ | R$^i$ | Reference |
|---|---|---|---|---|---|---|---|
| X.18 | C$_2$H$_5$ | CH$_2$CH=CHCl | 4-(OCH$_2$-C≡CH)-phenyl | H | H | H | EPA-137 174 |
| X.19 | C$_3$H$_7$ | C$_2$H$_5$ | 4-(CH$_2$OC$_2$H$_5$)-phenyl | H | H | H | EP-A 137 200 |
| X.20 | C$_3$H$_7$ | C$_2$H$_5$ | 3-Br-3-methyl-4-Br-tetrahydropyran-4-yl | H | H | H | EP-A 230 235 |
| X.21 | C$_3$H$_7$ | CH$_2$CH=CHCl | 3-Br-3-methyl-4-Br-tetrahydropyran-4-yl | H | H | H | EP-A 230 235 |
| X.22 | C$_3$H$_7$ | CH$_2$CH=CHCl | 2,6,6-trimethyl-cyclohex-1-en-1-yl | H | H | H | EP-A 46 860 |
| X.23 | C$_3$H$_7$ | C$_2$H$_5$ | 4-methylcyclohexyl | H | H | H | JP-A 540 191 945 |

TABLE B-continued

| No. | R$^d$ | R$^o$ | R$^f$ | R$^g$ | R$^h$ | R$^i$ | Reference |
|---|---|---|---|---|---|---|---|
| X.24 | C$_3$H$_7$ | C$_2$H$_5$ | (3-methylcyclohex-1-enyl) | H | H | H | EP-A 46 860 |
| X.25 | CH$_3$ | CH$_2$CH=CHCl | (4-methylcyclohexyl) | H | H | H | EP-A 88 299 |
| X.26 | C$_3$H$_7$ | C$_2$H$_5$ | (4-trifluoromethylphenyl) | H | H | K | EP-A 137 174 |
| X.27 | C$_2$H$_5$ | CH$_2$CH=CHCl | (2,6,6-trimethylcyclohex-1-enyl) | H | H | H | EP-A 46 860 |
| X.28 | C$_3$H$_7$ | CH$_2$CH=CHCH$_3$ | (2-methyl-thiazol-5-yl) | H | H | H | EP-A 125 094 |
| X.29 | C$_3$H$_7$ | CH$_2$CH=CHCl | (2-methyl-thiazol-5-yl) | H | H | H | EP-A 125 094 |

TABLE B-continued

[Structure: cyclohexenone with OR^i, =NOR^e substituent with R^d, R^f, R^g, R^h, and carbonyl]

| No. | R^d | R^e | R^f | R^g | R^h | R^i | Reference |
|---|---|---|---|---|---|---|---|
| X.30 | C3H7 | C2H5 | [3,5-dimethylcyclohexyl with H3C substituents] | H | H | H | EP-A 88 299 |
| X.31 | C3H7 | CH2CH=CH2 | [cyclohexyl with HO, H3C, and methyl substituents] | H | H | H | EP-A 228 598 |
| X.32 | C2H5 | C2H5 | [cyclohexyl with H5C2S and methyl substituents] | H | H | H | EP-A 228 598 |
| X.33 | C3H7 | C2H5 | [cyclohexyl with HO substituent] | H | H | H | EP-A 66 195 |
| X.34 | n-C3H7 | CH2CH=CHCl | [pyrazole with N—CH3] | H | H | H | EP-A 66195 |

TABLE B-continued $$\text{structure with } R^f, R^g, R^h, R^i, OR^i, NOR^e, R^d$$

| No. | $R^d$ | $R^e$ | $R^f$ | $R^g$ | $R^h$ | $R^i$ | Reference |
|---|---|---|---|---|---|---|---|
| X.35 | n-$C_3H_7$ | $CH_2CH=CH_2$ | (thiazole with $CH_3$) | H | H | H | EP-A 125 094 |
| X.36 | n-$C_3H_7$ | $C_3H_7$ | $CH(SCH_2CH_3)_2$ | H | H | H | EP-A 230 260 |
| X.37 | n-$C_3H_7$ | $C_2H_5$ | (3-methyltetrahydrothiopyran S=O) | H | H | H | EP-A 115 808 |
| X.38 | n-$C_3H_7$ | $C_2H_5$ | (3-methyltetrahydrothiopyran SO$_2$) | H | H | H | EP-A 115 808 |
| X.39 | n-$C_3H_7$ | $C_2H_5$ | $CH_3$ | $CH_3$ | H | H | EP-A 172 551 |
| X.40 | n-$C_3H_7$ | $CH_2CH=CH_2$ | (tetrahydrothiopyran SO$_2$) | OH | H | H | Proceedings Brit. Crop-Protection Conference - weeds 1985 Vol. 1 pages 93–98 |
| X.41 | n-$C_3H_7$ | $(CH_2)_2CH=CH$-(4-F-phenyl) | (tetrahydrothiopyran S) | H | H | H | DE-A 38 38 309 |

TABLE B-continued

![structure](cyclohexanone with OR^i, NOR^e, R^d, R^f, R^g, R^h substituents)

| No. | $R^d$ | $R^e$ | $R^f$ | $R^g$ | $R^h$ | $R^i$ | Reference |
|---|---|---|---|---|---|---|---|
| X.42 | $C_2H_5$ | $(CH_2)_2CH=CH$-(4-F-phenyl) | tetrahydrothiopyran-3-yl | H | H | H | DE-A 38 38 309 |
| X.43 | $C_2H_5$ | $(CH_2)_2CH=CH$-(4-Cl-phenyl) | tetrahydrothiopyran-3-yl | H | H | H | DE-A 38 38 309 |
| X.44 | $C_2H_5$ | $CH_2CH=CH-CH_2$-(4-Cl-phenyl) | tetrahydrothiopyran-3-yl | H | H | H | DE-A 38 38 309 |

Herbicidal active ingredients and antidote compounds can be applied together or separately after emergence to the leaves and shoots of the crops and of the undesirable grasses. Preferably, the antidote is applied simultaneously with the herbicidal active ingredient. Separate application is also possible, the antidote being applied to the field first, followed by the herbicidal active ingredient. The herbicidal active ingredient and the antidote may be formulated together or separately as sprays in suspendable, emulsifiable or soluble form.

Treatment of the seeds of the crops with the antidote prior to sowing is also important in practice. The herbicidal active ingredient is then applied alone in a conventional manner.

For herbicidal (hetaryloxy)-phenoxyacetic acid derivatives IX, different amounts of an antidote compound are required if the herbicide is used in different crops. The ratios can be varied within wide ranges. They are likewise dependent on the structure of the (hetaryloxy)phenoxyacetic acid derivatives IX and on the particular target crop. Suitable weight ratios of herbicidal active ingredients to antidote compound are from 1:10 to 1:0.01, preferably from 1:4 to 1:0.1.

For the same cyclohexenone derivative X, different amounts of an antidote compound are required if the cyclohexenone derivative X is used in different crops. The ratios in which a cyclohexenone derivative X and a cyanoquinoline IA or IB are used can be varied within wide ranges. They are dependent on the structure of the cyclohexenone derivative X and of the cyanoquinoline IA or IB and on the particular crop. Suitable weight ratios of herbicidal active ingredient to antidote compound are from 1:10 to 1:0.01, preferably from 1:4 to 1:0.25, both for application together and for application separately.

The novel herbicides may contain, in addition to the cyanoquinoline IA or IB as an antidote and the herbicide from the group consisting of the (hetaryloxy)phenoxyacetic acids IX or the cyclohexenones X, further herbicidal or growth-regulating active ingredients having a different chemical structure, the antagonistic effect being retained.

The novel agents or, in the case of separate application, the herbicidal active ingredients or the antidote are used, for example, in the form of directly sprayable solutions, powders, suspensions, including concentrated aqueous, oily or other suspensions or dispersions, emulsions, oil dispersions, pastes, dusting agents, broadcasting agents or granules, by spraying, atomizing, dusting, broadcasting or pouring. The application forms depend entirely on the intended uses.

For the preparation of directly sprayable solutions, emulsions, pastes and oil dispersions, mineral oil fractions of medium to high boiling point, such as kerosene or diesel oil, coal tar oils and oils of vegetable or animal origin, aliphatic, cyclic or aromatic hydrocarbons, e.g. benzene, toluene, xylene, paraffin, tetrahydronaphthalene, alkylated naphthalenes or derivatives thereof, for example, methanol, ethanol, propanol, butanol, chloroform, carbon tetrachloride, cyclohexanol, cyclohexanone, chlorobenzene or isophorone, and strongly polar solvents, e.g. dimethylformamide, dimethyl sulfoxide, N-methylpyrrolidone and water, are suitable.

Aqueous application forms can be prepared from emulsion concentrates, pastes, wettable powders or oil dispersions by adding water. For the preparation of emulsions, pastes or oil dispersions, the herbicidal active ingredient and/or the antidote, as such or in solution in an oil or solvent, can be homogenized in water by means of wetting agents, adhesives, dispersants or emulsifiers. However, it is also possible to prepare concentrates which consist of the herbicidal active ingredient and/or antidote, wetting agent, tackifiers, dispersants or emulsifiers and, if required, solvents or oil and which are suitable for dilution with water.

Suitable surfactants are alkali metal, alkaline earth metal and ammonium salts of ligninsulfonic acid, naphthalenesulfonic acid, phenolsulfonic acid, alkylarylsulfonates, alkylsulfates, alkylsulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols and octadecanols, salts of sulfated fatty alcohol glycol ethers, condensates of sulfonated naphthalenes and naphthalene derivatives with formaldehyde, condensates of naphthalene or of naphthalenesulfonic acids with phenol and formaldehyde, polyoxyethylene octylphenol ether, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders, broadcasting agents and dusting agents can be prepared by mixing or milling the herbicidal active ingredient and/or the antidote together with a solid carrier.

Granules, for example coated, impregnated and homogeneous granules, can be prepared by binding the active ingredients to solid carriers. Examples of solid carriers are mineral earths, such as silica gel, silicas, silicates, talc, kaolin, attaclay, limestone, chalk, bole, loess, clay, dolomite, kieselguhr, calcium sulfate, magnesium sulfate, magnesium oxide, milled plastics, fertilizers, e.g. ammonium sulfate, ammonium phosphate, ammonium nitrate or ureas, and vegetable products, such as cereal meals, ground bark, woodmeal and nutshell meal, cellulose powder and other solid carriers.

The formulations contain from 0.1 to 95, preferably from 0.5 to 90, % by weight of herbicidal active ingredient and antidote. The application rates of herbicidal active ingredient are from 0.2 to 5 kg/ha of active substance (a.s.).

The Examples which follow illustrate the preparation of the novel compounds.

PREPARATION EXAMPLES

EXAMPLE 1

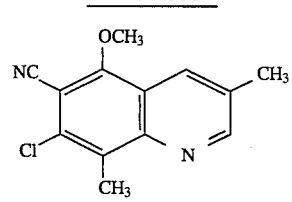

A mixture of 3.8 g (0.02 mol) of 7-chloro-3,8 -dimethyl-5-nitroquinoline, 2.6 g (0.04 mol) of potassium cyanide and 150 ml of methanol was refluxed for 15 hours. Thereafter, water was added to the reaction mixture and extraction was carried out with methylene chloride. 1.5 g (38%) of the product of melting point 173°–174° C. (active ingredient example 4.001) were obtained from the organic phase after chromatographic purification.

EXAMPLE 2

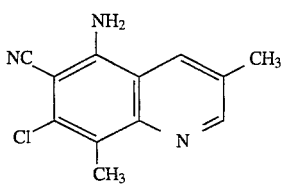

A mixture of 11.8 g (0.05 mol) of 7-chloro-3,8-dimethyl-5-nitroquinoline, 150 ml of dimethylformamide (anhydrous), 16 ml (0.15 mol) of ethyl cyanoacetate, 5.5 g (0.10 mol) of potassium hydroxide and 3.3 g (0.05 mol) of potassium cyanide was left for 15 hours at 50° C. Thereafter, the solvent was distilled off under reduced pressure and the resulting residue was kept for 0.5 hour at 80° C. with 100 ml of 5% strength aqueous sodium hydroxide solution. The product was precipitated as a solid on cooling.

Yield: 8.4 g (72%); mp.: 260°–265° C.; active ingredient example 4.002

EXAMPLE 3

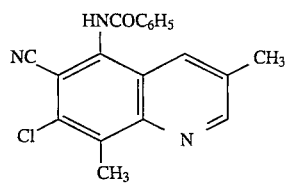

A mixture of 6.95 g (0.03 mol) of the product from Example 2, 100 ml of pyridine, 0.5 g of 4-N,N-dimethylaminopyridine and 5.0 ml (0.04 mol) of benzoyl chloride was left for 40 hours at 80° C. The reaction mixture was then mixed with 400 ml of 5% strength hydrochloric acid, the product being precipitated as a solid.

Yield: 3.6 g (36%); mp.: >240° C.; active ingredient example 4.003

EXAMPLE 4

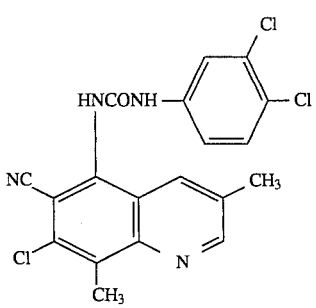

A mixture of 5.8 g (0.025 mol) of the product from Example 2, 100 ml of nitrobenzene, 5.64 g (0.04 mol) of 3,4-dichlorophenyl isocyanate and 2.16 g (0.04 mol) of sodium methylate was left for 4 hours at 80° C. The product was precipitated as a solid on cooling.

Yield: 4.3 g (41%); mp.: 215°–218° C.; active ingredient example 4.004

EXAMPLE 5

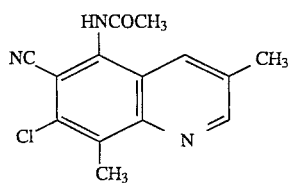

A mixture of 6.95 g (0.03 mol) of the product from Example 2 and 50 ml of acetic anhydride was refluxed for 20 hours at 120° C. The product was precipitated as a solid when the reaction mixture was cooled.

Yield: 7.0 g (98%); mp.: 220°–225° C.; active ingredient example 4.005

EXAMPLE 6

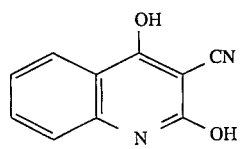

81.5 g (0.50 mol) of isatoic anhydride were added dropwise to a solution of 54.5 g (0.55 mol) of methyl cyanoacetate and 56 g (0.55 mol) of triethylamine in 50 ml of dimethylformamide and the mixture was stirred for 4 hours at 80° C. After the addition of 60 g of sodium carbonate in 400 ml of water, the mixture was refluxed for 2 hours. On addition of 250 ml of concentrated hydrochloric acid, the product was precipitated as a solid.

Yield: 80 g (85%); mp.: >250° C.

EXAMPLE 7

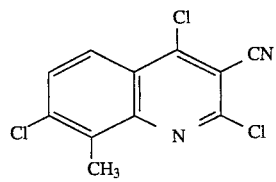

A mixture of 60 g (0.38 mol) of phosphorus oxychloride, 15 g (0.14 mol) of triethylamine and 33.5 g (0.15 mol) of 7-chloro-3-cyano-2,4-dihydroxy-8-methylquinoline was refluxed for 6 hours. After cooling and hydrolysis of the reaction mixture with 500 g of ice, 21 g (55%) of a solid product of melting point 135° C. were isolated.

EXAMPLE 8

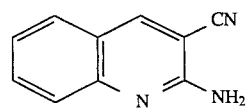

60.5 g (0.5 mol) of o-aminobenzaldehyde and 35 g (0.53 mol) of malodinitrile in 500 ml of ethanol were heated at the boil with 1 ml of pyridine for 3 hours. After cooling, 72.5 g (86%) of the solid product of melting point 235° C. were precipitated. Reference: E. C. Taylor and N. W. Kalenda, J. Org. Chem. 18 (1953), 1755

The active ingredients listed in the Tables below can be prepared by processes similar to these Examples.

TABLE 1

Structure: quinoline with $R_m^1$ on benzene ring, CN at 3-position, $R^2$ at 2-position

| Example no. | $R_m^1$ | $R^2$ | Physical data [mp (°C.)] |
|---|---|---|---|
| 1.001 | H | NHCOCH₃ | 209 |
| 1.002 | H | NHCOCH₂COCH₃ | 253 |
| 1.003 | H | NHCONHCH₂CH₂CH₃ | 180 |
| 1.004 | H | NHCONHCH(CH₃)₂ | 207–210 |
| 1.005 | H | NHCONHC₆H₅ | 183 |
| 1.006 | H | NH—(CH₂)₃—N(pyrrolidinyl) | 103–105 |
| 1.007 | H | NH—(CH₂)₃—OCH₃ | 115 |
| 1.008 | H | NHN(CH₃)₂ | 212 |
| 1.009 | H | piperazinyl-NCH₂CH₂NH₂ | 150 |
| 1.010 | H | pyrrolidinyl (N-linked) | 155 |
| 1.011 | H | pyrrolyl with HCO | 178–180 |
| 1.012 | H | N=CHN(CH₃)₂ | 237–240 |
| 1.013 | 4-OH | OH | >250 |
| 1.014 | 4,7-Cl₂, 8-CH₃ | Cl | 135 |
| 1.015 | 6-Br, 4-Cl | Cl | 185 |
| 1.016 | 5-Cl, 4-OH | Cl | 180 |
| 1.017 | H | CN | |

TABLE 2

Structure: quinoline with $R_m^1$ on benzene ring, $R^2$ at 4-position, CN at 3-position

| Example no. | $R_m^1$ | $R^2$ | Physical data [mp. (°C.)] |
|---|---|---|---|
| 2.001 | 2-Cl | NHN(CH₃)₂ | 275 |
| 2.002 | 2-Cl | NH—(CH₂)—OCH₃ | 271 |
| 2.003 | 2-Cl | NHCH₂CO₂CH₂CH₃ | 140 |
| 2.004 | 2-Cl | N(CH₂CH₂CH₃)₂ | 83–85 |
| 2.005 | 2-Cl | N(CH₂CH₃)₂ | 135–139 |
| 2.006 | 2-Cl | NH—(CH₂)₃—N(pyrrolidinyl) | 137–140 |
| 2.007 | 2-Cl | NH—(CH₂)₃—N(imidazolyl) | 208–210 |
| 2.008 | 2-Cl | N(CH₂CH₂OH)₂ | 172–175 |
| 2.009 | 2-Cl | N(pyrrolidinyl) | 143–145 |

TABLE 3

Structure: quinoline with CN, $R_m^1$, and $R^2$ substituents

| Example no. | $R_m^1$ | $R^2$ | Physical data [mp. (°C.)] |
|---|---|---|---|
| 3.001 | 2,6-(CH₃)₂ | H | 69–71 |
| 3.002 | 3,8-(CH₃)₂ | 7-Cl | 190 |
| 3.003 | 6-NH(CH₂)₂NH₂ | H | |

TABLE 4

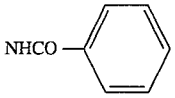

| Example no. | $R_m^1$ | $R^2$ | Physical data [mp. (°C.)] |
|---|---|---|---|
| 4.001 | 7-Cl, 3,8-(CH$_3$)$_2$ | OCH$_3$ | 173–174 |
| 4.002 | 7-Cl, 3,8-(CH$_3$)$_2$ | NH$_2$ | 260–265 |
| 4.003 | 7-Cl, 3,8-(CH$_3$)$_2$ | NHCO–C$_6$H$_5$ | >240 |
| 4.004 | 7-Cl, 3,8-(CH$_3$)$_2$ | NHCONH–(3,4-Cl$_2$-C$_6$H$_3$) | 215–218 |
| 4.005 | 7-Cl, 3,8-(CH$_3$)$_2$ | NHCOCH$_3$ | 220–225 |
| 4.006 | 8-CH$_3$ | NH$_2$ | 220–224 |
| 4.007 | 2,8-(CH$_3$)$_2$ | NH$_2$ | 218–220 |
| 4.008 | 7-Cl, 8-CH$_3$ | NH$_2$ | >260 |
| 4.009 | 7,8-(CH$_3$)$_2$ | NH$_2$ | 233–235 |
| 4.010 | 7-Cl, 3,8-(CH$_3$)$_2$ | NH–CO–CH$_2$–CH$_3$ | 218–222 |
| 4.011 | 7-Cl, 3,8-(CH$_3$)$_2$ | NH–CO-(4-NO$_2$–C$_6$H$_4$) | >260 |
| 4.012 | 7-Cl, 8-CH$_3$ | NH–CO-(2,6-Cl$_2$–C$_6$H$_3$) | >260 |
| 4.013 | 2-(CH$_2$)$_2$CH$_3$, 3-C$_2$H$_5$ | NH–CO–COOC$_2$H$_5$ | 170–174 |
| 4.014 | 3,8-(CH$_3$)$_2$ | N=CH-(4-Cl–C$_6$H$_4$) | 200–202 |
| 4.015 | 7-Cl, 3,8-(CH$_3$)$_2$ | Cl | 148–151 |
| 4.016 | 7-Cl, 3,8-(CH$_3$)$_2$ | Br | 162–164 |
| 4.017 | 7-Cl, 8-CH$_3$ | OCH$_3$ | 236–240 |
| 4.018 | 8-CH$_3$ | CH$_3$ | 182 |

TABLE 5

[Structure: quinoline with CN group and R² substituent, and R¹ₘ on benzene ring]

| Example no. | R¹ₘ | R² | Physical data [mp. (°C.)] |
|---|---|---|---|
| 5.001 | 2-OCH₃ | H | 108–110 |
| 5.002 | 2-CH₃ | H | 140 |
| 5.003 | 2-NH—CH=N- (linked to another quinoline with NC) | H | >260 |
| 5.004 | 2-C₆H₅ | H | 187 |
| 5.005 | 2-(4-Cl—C₆H₄) | H | 187 |
| 5.006 | 2-(3,5-dimethyl-pyrrol-4-yl), NH | H | 93–96 |
| 5.007 | 2-(1,3,5-trimethyl-pyrrol-4-yl) | H | 177–184 |
| 5.008 | 2-(1,3,5-trimethyl-pyrrol-4-yl with CH=CH-NO₂) | H | >240 |
| 5.009 | 2-(1-benzyl-3,5-dimethyl-pyrrol-4-yl) | H | 102–105 |
| 5.010 | 6-NO₂, 2-CH₃ | H | 205 |
| 5.011 | 7-NO₂, 2,6-Cl₂ | H | |
| 5.012 | 2-Cl | 4-NH₂ | |
| 5.013 | 2-CH₃ | 4-NH₂ | |
| 5.014 | 2-OCH₃ | 4-NH₂ | |
| 5.015 | 2-Cl | 4-NH—CH(CH₃)₂ | |
| 5.016 | 2-CH₃ | 4-NH—CO—CH₃ | |
| 5.017 | 2-N(piperidinyl) | 4-N(piperidinyl) | 147–150 |
| 5.018 | 2-N(morpholinyl) | 4-N(morpholinyl) | |
| 5.019 | 2-Cl | 4-OCH₃ | |
| 5.020 | 2-Cl | 4-O—CH₂CH₃ | |
| 5.021 | 2-Cl | 6,7-(OCH₃)₂, 4-Cl | 230 |
| 5.022 | 2-OCH₃ | 4-OCH₃ | |
| 5.023 | H | 5-S—S—(3-methyl-4-nitrophenyl) | 206 |
| 5.024 | 2-Cl | 4-S—C₆H₅ | |

TABLE 5-continued

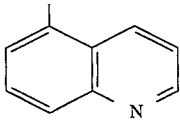

| Example no. | $R_m^1$ | $R^2$ | Physical data [mp. (°C.)] |
|---|---|---|---|
| 5.025 | 2-Cl | 4-SO$_2$—C$_6$H$_5$ | |
| 5.026 | 2-Cl | 4-SO$_2$—CH$_3$ | 225 |
| 5.027 | 2-Cl | 4,6,8-Cl$_3$ | 182 |
| 5.028 | 2-Cl | 4,6,8-Cl$_3$, 7-Br | 90–94 |
| 5.029 | 2-Cl | 4-Cl, 6,8-Br$_2$ | 180 |
| 5.030 | 2-F | 4-F, 6,8-Cl$_2$ | >260 |
| 5.031 | 2-NH$_2$ | 8-CH=C(CN)$_2$ | >260 |
| 5.032 | 2-NH$_2$ | 8-CH=N—N=CH— (5-quinolinyl) | >260 |
| 5.033 | H | 3,8-(CH$_3$)$_2$, 5-CN | |
| 5.034 | 7-Cl | 3,8-(CH$_3$)$_2$, 5-CN | 134–137 |

TABLE 6

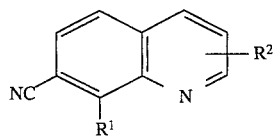

| Example no. | $R^1$ | $R^2$ | mp. [°C.] |
|---|---|---|---|
| 6.001 | NH$_2$ | H | 148–150 |
| 6.002 | NH$_2$ | 3-CH$_3$ | 198–204 |
| 6.003 | CH$_3$ | H | 129–131 |
| 6.004 | CH$_3$ | 3-CH$_3$ | 125–126 |
| 6.005 | CH$_2$Br | H | 120–122 |
| 6.006 | CH$_2$Br | 3-CH$_3$ | |
| 6.007 | CH$_2$—CN | H | 161–163 |
| 6.008 | CH$_2$—COOCH$_3$ | H | 115–117 |
| 6.009 | CH$_2$—COOCH$_3$ | 3-CH$_3$ | |

TABLE 7

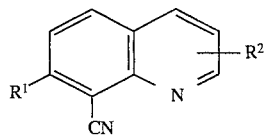

| Example no. | $R^1$ | $R^2$ | mp. [°C.] |
|---|---|---|---|
| 7.001 | NH$_2$ | 3-Cl | 245 |
| 7.002 | NH—(CH$_2$)$_2$CH$_3$ | H | |
| 7.003 | NH—(CH$_2$)$_3$CH$_3$ | H | |
| 7.004 | NH—(CH$_2$)$_4$CH$_3$ | H | 81 |
| 7.005 | —N(CH$_2$CH$_2$)$_2$N—CH$_3$ (piperazinyl) | H | 152 |
| 7.006 | —N(CH$_2$CH$_2$)$_2$O (morpholinyl) | H | 127 |

TABLE 7-continued

| Example no. | $R^1$ | $R^2$ | mp. [°C.] |
|---|---|---|---|
| 7.007 | —O—(3-CF$_3$-4-NH$_2$-C$_6$H$_3$) | 3-Cl | 169 |
| 7.008 | —S—CH$_2$—COOCH$_3$ | 3-Cl | 100 |
| 7.009 | CH$_3$ | 3-CH$_3$ | 148–150 |

Table I below lists cyanoquinoline compounds which are known from the literature and are likewise capable of increasing the toleration of the herbicidal active ingredients of the formulae IX and X by crops.

TABLE I

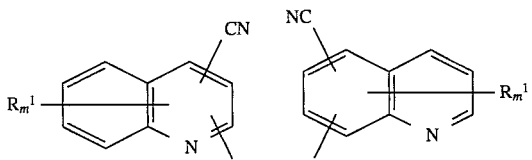

| Example | Position of CN | $R_m^1$ | $R^2$ | Reference |
|---|---|---|---|---|
| I.001 | 3 | H | 2-NH$_2$ | 1 |
| I.002 | 3 | H | 2-OH | 2 |
| I.003 | 4 | H | 3-NH$_2$ | 3 |
| I.004 | 4 | 5-OCH$_3$ | H | 4 |
| I.005 | 5 | 6-OCH$_3$ | H | 4 |

1) T. Higashino, H. Ito and E. Hayashi, Chem. Pharm. Bull. 20 (1972), 1544

2) Coutts, J. Chem. Soc. C, 1969, 713

3) Y. Tomioka, K. Ohkubo and M. Yamazaki, Chem. Pharm. Bull. 33 (1985), 1360

4) T. Okamoto, H. Takahashi, H. Takayama, T. Kitagawa and M. Ikeda, Chem. Pharm. Bull. 17 (1969), 140

EXAMPLES OF BIOLOGICAL ACTION

The effect of various members of the novel herbicides or combinations of agents, consisting of a herbicide and an antidote compound, on the growth of desired and undesirable plants compared with the herbicidal active ingredient alone is demonstrated by the following biological examples of greenhouse experiments.

The culture vessels used were plastic flowerpots having a capacity of about 300 cm³ containing loamy sand with about 3.0% humus as a substrate. The seeds of the test plants were sown shallowly and separately according to species and were moistened. Thereafter, the vessels were covered with transparent plastic covers until the seeds uniformly germinated and the plants had begun to grow.

For the postemergence treatment, the test plants were first grown to a height of growth of from 3 to 20 cm, depending on the form of growth, and were treated only thereafter. The herbicides were suspended or emulsified in water as a distributing agent and were sprayed by means of finely distributing nozzles.

The test vessels were placed in a greenhouse, from 18° to 30° C. being preferred for heat-loving species and from 10° to 25° C. being preferred for those of more temperate climates.

The test period extended over from 3 to 5 weeks. During this time, the plants were tended and their reaction to the individual treatments was recorded.

The damage to the test plants was evaluated on the basis of a scale from 0 to 100% in comparison with the untreated control plants. 0 means no damage and 100 means complete destruction of the plants.

The plants used in the greenhouse experiments consisted of the following species:

| Botanical name | Common name |
| --- | --- |
| Brachiaria platyphylla | |
| Lolium multiflorum | Italian ryegrass |
| Oryza sativa | rice |
| Setaria faberii | millet |
| Setaria italica | Italian millet |
| Triticum aestivum | summer wheat |
| Zea mays | corn |

X.2 was used as an example of a herbicide based on the cyclohexenone derivatives of the formula X. The herbicidal active ingredient X.2 was added to the spray liquor as a commercially formulated product (with 184 g/l of EC, and alone, in each case with the addition of the appropriate amount of solvent system XXII (blank formulation)) and applied together with the antidote compound.

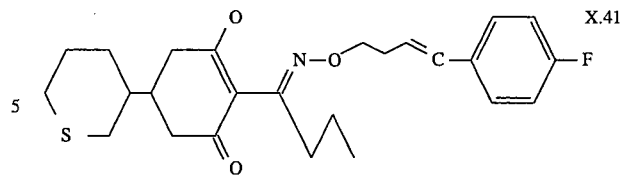

was used as a further example of the herbicidal cyclohexenone derivatives of the formula X.

The active ingredient X.41 was applied as an emulsion concentrate with 200 g of active ingredient/l, likewise alone with the addition of the amount of solvent required for the antidote, 80% of cyclohexenone and 20% of Emulphor EL with 10% by weight of active ingredient.

For the postemergence treatment, all antidote compounds were, prepared as a mixture consisting of 80% of cyclohexenone and 20% of Emulphor EL with 10% by weight of active ingredient.

The Tables below document the antidote action of the novel compounds 1.017, 3.003, 4.002, 4.008, 5.014, 6.002 and 7.007.

The compounds substantially improve the toleration of active ingredient X.2 and of active ingredient X.41 by the crops belonging to the Gramineae family (grasses).

TABLE A

Improvement of the toleration of herbicidal active ingredient X.2 by crops through combination with compound 1.017 in postemergence application in the greenhouse

| Application rate [kg/ha a.s.] | | Test plants and damage [%] | | |
| --- | --- | --- | --- | --- |
| Herbicidal active ingredient X.2 | Antidote 1.017 | Crop Triticum aestivum[1] | Undesirable plants Lolium multiflorum | Setaria italica |
| 0.06 | — | 35 | 100 | 90 |
| 0.06 | 0.25 | 10 | 100 | 90 |

[1] cv. "Star"

TABLE B

Improvement of the toleration of herbicidal active ingredient X.2 by crops through combination with compound 3.003 in postemergence application in the greenhouse

| Application rate [kg/ha a.s.] | | Test plants and damage [%] | | | |
| --- | --- | --- | --- | --- | --- |
| Herbicidal active ingredient X.2 | Antidote 3.003 | Crops Oryza sativa[1] | Triticum aestivum[2] | Undesirable plants Lolium multiflorum | Setaria italica |
| 0.03 | — | 50 | 30 | 100 | 98 |
| 0.03 | 0.125 | 10 | 10 | 100 | 95 |

[1] cv. "Bahia"
[2] cv. "Star"

TABLE C

Improvement of the toleration of herbicidal active ingredient X.2 by crops through combination with compound 4.006 in postemergence application in the greenhouse

| Application rate [kg/ha a.s.] | | Test plants and damage [%] | | | |
|---|---|---|---|---|---|
| Herbicidal | | | Undesirable plants | | |
| active ingredient X.2 | Antidote 4.008 | Crop Oryza sativa[1] | Brachiaria plat. | Lolium multiflorum | Setaria italica |
| 0.03 | — | 50 | 85 | 100 | 98 |
| 0.03 | 0.125 | 15 | 80 | 100 | 98 |

[1] cv. "Bahia"

TABLE D

Improvement of the toleration of herbicidal active ingredient X.2 by crops through combination with compound 5.014 in postemergence application in the greenhouse

| Application rate [kg/ha a.s.] | | Test plants and damage [%] | | |
|---|---|---|---|---|
| Herbicidal | | | Undesirable plants | |
| active ingredient X.2 | Antidote 5.014 | Crop Oryza sativa[1] | Brachiaria plat. | Lolium multiflorum |
| 0.06 | — | 90 | 90 | 100 |
| 0.06 | 0.25 | 10 | 100 | 100 |

[1] cv. "Bahia"

TABLE E

Improvement of the toleration of herbicidal active ingredient X.2 by crops through combination with compound 6.002 in postemergence application in the greenhouse

| Application rate [kg/ha a.s.] | | Test plants and damage [%] | | |
|---|---|---|---|---|
| Herbicidal | | | Undesirable plants | |
| active ingredient X.2 | Antidote 6.002 | Crop Oryza sativa[1] | Brachiaria plat. | Lolium multiflorum |
| 0.06 | — | 90 | 90 | 100 |
| 0.06 | 0.25 | 15 | 80 | 100 |

[1] cv. "Bahia"

TABLE F

Improvement of the toleration of herbicidal active ingredient X.2 by crops through combination with compound 7.007 in postemergence application in the greenhouse

| Application rate [kg/ha a.s.] | | Test plants and damage [%] | |
|---|---|---|---|
| Herbicidal active ingredient X.2 | Antidote 7.007 | Crop Oryza sativa[1] | Undesirable plant Setaria italica |
| 0.03 | — | 50 | 98 |
| 0.06 | 0.125 | 0 | 95 |

[1] cv. "Bahia"

TABLE G

Improvement of the toleration of herbicidal active ingredient X.2 by crops through combination with compound 7.007 in postemergence application in the greenhouse

| Application rate [kg/ha a.s.] | | Test plants and damage [%] | | |
|---|---|---|---|---|
| Herbicidal active | | | Undesirable plants | |
| ingredient X.2 | Antidote 7.007 | Crop Zea mays[1] | Lolium multiflorum | Setaria italica |
| 0.06 | — | 100 | 100 | 100 |
| 0.06 | 0.25 | 20 | 100 | 95 |

[1] cv. "Mutin"

TABLE H

Improvement of the toleration of herbicidal active ingredient X.41 by crops through combination with compound 4.002 in postemergence application in the greenhouse

| Application rate [kg/ha a.s.] | | Test plants and damage [%] | | |
|---|---|---|---|---|
| Herbicidal active | | | Undesirable plants | |
| ingredient X.2 | Antidote 4.002 | Crop Zea mays | Setaria faberil | Setaria italica |
| 0.125 | — | 40 | 90 | 85 |
| 0.125 | 0.5 | 10 | 80 | 80 |

We claim:
1. A herbicidal composition containing one or more cyanoquinoline compounds of the formula IA or IB

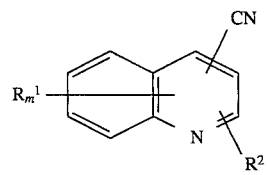

Ia

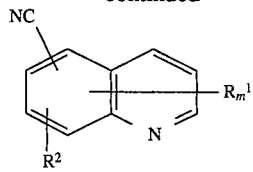

where $R^1$ is $CH=C(CN)_2$; $CH=N-N-CH-$(5-quinolinyl); methylsulfonyl; $CH=NOH$; halogen; nitro; cyano; $C_1-C_4$-alkyl which is unsubstituted or monosubstituted by cyano, hydroxyl, carboxyl, or $C_1-C_4$-alkoxycarbonyl; $C_1-C_4$-haloalkyl; $C_1-C_4$-alkoxy; $C_1-C_4$-haloalkoxy, $C_1-C_4$-alkylthio which is unsubstituted or monosubstituted by $C_1-C_4$-alkoxycarbonyl; pyrrolidinyl; piperidinyl; morpholinyl; thiomorpholinyl; phenyl, phenoxy, phenylthio, phenyldithiolyl, phenylsulfonyl or pyrrolyl which may carry from one to three of the following groups: halogen, $C_1-C_4$-alkyl, $C_1-C_4$-haloalkyl, $C_1-C_4$-alkoxy, $C_1-C_4$-alkylthio, $C_2-C_4$-alkenyl, nitro, amino, nitro-$C_2-C_4$-alkenyl or benzyl; m is 0, 1, 2 or 3, and the radicals $R^1$ my be different when m is 2 or 3;

$R^2$ is hydrogen; $C_1-C_4$-alkoxy; $-NR^3R^4$; $-NR^5-CXR^6$ or $-N=CR^7R^8$;

$R^3$ is hydrogen or $C_1-C_4$-alkyl which may carry from one to five halogen atoms and/or one of the following groups: hydroxyl, $C_1-C_4$-alkoxy, $C_1-C_4$-haloalkoxy, $C_1-C_4$-alkylthio, amino, $C_1-C_4$-alkylamino or di-$C_1-C_4$-alkylamino;

$R^4$ is one of the groups stated for $R^3$; $C_1-C_4$-alkylamino, di-$C_1-C_4$-alkylamino; $C_1-C_4$-alkyl which carries one of the following radicals: $C_1-C_4$-alkoxycarbonyl, 1-pyrrolidinyl or 1-imidazolyl; $CH=N-$(3-cyano-2-quinolinyl);

or $R^3$ and $R^4$ together form a $C_4$- or $C_5$-alkylene chain which may be interrupted by an oxygen or nitrogen member, where the nitrogen atom in turn may carry a $C_1-C_4$-alkyl or amino-$C_1C_4$-alkyl group, or a 1,3-butadienyl chain which may carry one or two of the radicals stated for $R^1$ or formyl;

$R^5$ is hydrogen or $C_1-C_4$-alkyl;

$R^6$ is one of the groups stated for $R^5$, $C_1-C_4$-alkyl which carries one of the following radicals: $C_1-C_4$-alkoxy, $C_1-C_4$-alkylcarbonyl or $C_1-C_4$-alkoxycarbonyl; $C_3-C_7$-cycloalkyl; $C_1-C_4$-alkoxycarbonyl; a phenyl ring which may carry from one to three of the groups stated for $R^1$; amino, $C_1-C_4$-alkylamino, di-$C_1-C_4$-alkylamino; $C_3-C_7$-cycloalkylamino or phenylamino, where the aromatic ring may carry from one to three of the groups stated for $R^1$;

X is oxygen or sulfur;

$R^7$ is one of the groups stated for $R^5$;

$R^8$ is one of the groups stated for $R^6$;

and the agriculturally usable salts of the compounds IA and IB, provided that these compounds contain a basic nitrogen substituent or an acidic hydroxyl substituent, and a cyclohexenone oxime ether of the formula

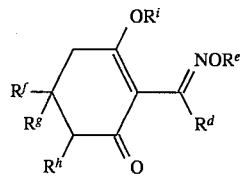

where $R^d$ is $C_1-C_4$-alkyl;

$R^e$ is $C_1-C_4$-alkyl, $C_3$- or $C_4$-alkenyl, $C_3$- or $C_4$-haloalkylene or thenyl, which may be substituted by a halogen atom, $C_3$- or $C_4$-alkenyl, which carries a phenyl radical which may carry one radical: halogen;

$R^f$ is $C_1-C_4$-alkyl which may be monosubstituted by $C_1-C_4$-alkylthio; a 6-membered saturated ring system which, in addition to carbon members, may contain an oxygen or sulfur atom; phenyl or isoxazolyl radical which may carry up to three of the following groups: $C_1-C_4$-alkyl;

$R^g$ is hydrogen or, if $R^f$ is $C_1-C_6$-alkyl, a $C_1-C_6$-alkyl group;

$R^h$ is hydrogen, and $R^i$ is hydrogen or one equivalent of an environmentally compatible cation.

2. A herbicidal composition as in claim 1, wherein the weight ratio of cyanoquinoline compound IA or IB to herbicidal active ingredient a) or b) is from 0.01:1 to 10:1.

3. A herbicidal composition according to claim 1, containing compounds IA wherein the CN radical is in the 3-position and where $R^1$ is in a position ortho to the CN radical and denotes nitro, cyano, $C_1-C_4$-alkyl or $C_1-C_4$-alkoxy;

$R^2$ is in the other ortho positions to the CN radical and denotes hydrogen or $NH_2$; and m is 0 or 1.

4. A herbicidal composition according to claim 1, containing compounds IB wherein the CN radical is in the 5, 6, 7 or 8-position $R^1$ is nitro, cyano, $C_1-C_4$-alkyl or $C_1-C_4$-alkoxy;

$R^2$ is in one of the ortho positions to the CN radical and denotes hydrogen, $NHR^3$ or a phenoxy radical, where the phenyl ring may carry from one to three of the following groups: amino, halogen, $C_1-C_4$-alkyl $C_1-C_4$-haloalkyl, $C_1C_4$-alkoxy or $C_1-C_4$-alkylthio;

$R_3$ is hydrogen or $C_1-C_4$-alkyl which may carry from one to five halogen atoms and/or one of the following groups: hydroxyl, $C_1-C_4$-alkoxy, $C_1-C_4$-haloalkoxy, $C_1-C_4$-alkylthio, amino, $C_1-C_4$-alkylamino or di-$C_1-C_4$-alkylamino; and m is 0, 1, 2 or 3.

5. A herbicidal composition of the formula IA or IB according to claim 1, wherein the cyano group and the radical $R^2$ are positioned at adjacent ring carbon atoms.

6. A herbicidal composition of the formula IA or IB according to claim 1, wherein $R^2$ denotes $-NR^3R^4$, $-NR^5-CXR^6$ or $-N=CR^7R^8$.

7. A herbicidal composition of the formula IA or IB according to claim 1, wherein $R^1$ is cyano, $C_1-C_4$-alkyl which is unsubstituted or monosubstituted by cyano, hydroxyl, carboxyl or $C_1-C_4$-alkoxycarbonyl, $C_1-C_4$-haloalkyl, $C_1-C_4$-alkoxy, $C_1-C_4$-haloalkoxy, $C_1-C_4$-alkylthio which is unsubstituted or monosubstituted by $C_1-C_4$-alkoxycarbonyl; pyrrolidinyl; piperidinyl; morpholinyl or thiomorpholinyl.

* * * * *

UNITED STATES PATENT AND TRADEMARK OFFICE
CERTIFICATE OF CORRECTION

PATENT NO.: 5,565,408

DATED: October 15, 1996

INVENTOR(S): HAGEN et al.

It is certified that error appears in the above-identified patent and that said Letters Patent is hereby corrected as shown below:

On the cover page, item [57], line 17 after the formulae, "$C_3$-alkylene" should be --$C_5$-alkylene--; in both formula Ia and Ib after line 1 of the abstract, "$R_m^1$" should be --$R^1_m$--.

Column 38, claim 1, line 60, in formula Ia, "$R_m^1$" should be --$R^1_m$--.

Column 39, claim 1, line 1, in formula Ib, "$R_m^1$" should be --$R^1_m$--.

Signed and Sealed this

Twenty-eighth Day of January, 1997

Attest:

BRUCE LEHMAN

Attesting Officer     Commissioner of Patents and Trademarks